United States Patent [19]
Greene

[11] Patent Number: 5,627,319
[45] Date of Patent: May 6, 1997

[54] MOTION ACOUSTIC HOLOGRAPH

[76] Inventor: Ronald J. Greene, 29301 Carmel Rd., Sun City, Calif. 92586

[21] Appl. No.: 599,802

[22] Filed: Feb. 12, 1996

[51] Int. Cl.$^6$ ............ G01N 29/22; G03B 42/06
[52] U.S. Cl. ............................ 73/605; 73/603
[58] Field of Search ............ 73/603, 604, 605, 73/625, 626, 602; 367/8, 104, 11, 7; 364/821

[56] References Cited

U.S. PATENT DOCUMENTS

| | | |
|---|---|---|
| 3,685,008 | 8/1972 | Bhuta et al. . |
| 3,715,482 | 2/1973 | Haines et al. ............... 367/8 |
| 3,717,843 | 2/1973 | Farrah et al. . |
| 4,077,253 | 3/1978 | Grisell .................... 73/603 |
| 4,415,996 | 11/1983 | Maynard et al. ............ 367/8 |
| 4,817,434 | 4/1989 | Anderson ................. 73/625 |
| 5,384,573 | 1/1995 | Turpin ................... 342/179 |

*Primary Examiner*—Hezron E. Williams
*Assistant Examiner*—Rose M. Finley

[57] ABSTRACT

A new method of Acoustic Holography permits moving 3-D scenes by replacing a fixed film record of an interference pattern with a "live interference pattern" which is continuously altered by the information on a rotating CD.

15 Claims, 5 Drawing Sheets

FIG 6

FIG 7 VERTICAL WAVE AMPLIFICATION CIRCUITS

MOTION ACOUSTIC HOLOGRAPH

BACKGROUND OF THE INVENTION

1. Field of the Invention

This Invention relates to an acoustic wave interfering device for generating, decoding and illuminating acoustic holograms and more particularly for the generation, decoding and illumination of moving acoustic holograms from the frequency, amplitude and phase distribution information present on conventional analogue records, tapes and CD's.

2. Prior Art

Holography as conventionally used is a kind of three-dimensional lensless photography that records the interference pattern created by two highly coherent beams. Conventional holograms are therefore fixed records of interference patterns. Their use involves a two-step process; first, the freezing of the interference pattern in-time and second, its unfreezing or illumination. In the past, film has been used as the recording medium but during the exposure period all movement must be kept well below one-thousandth of a millimeter or be completely smudged. Fixed film holograms are therefore difficult to make, the object to be photographed usually having to be placed on a several-ton block of stone. The further development of "motion holography", the recording and displaying of moving images by film holography has been problematical with only the simplest forms of animated film holograms having been demonstrated.

This invention show how "motion holography" can be done in the acoustic range without the use of film as a storage medium. Acoustic holography now provides a unique solution to the "motion problem" by replacing the fixed film record of an interference pattern with a "live" interference pattern which can be continuously altered by the information stored on a rotating disk.

In this new acoustic motion holography process in the first step or freezing, the generation of the 3-D interference pattern is delayed and only the one-dimensional information about the wave, its frequency, amplitude and phase is frozen in-time and recorded. The second step or unfreezing, done at a later time then requires the simultaneous generation, decoding and illumination of the "live" 3-D interference pattern by causing two identical sets of highly coherent one-dimensional waves to interfere while being simultaneously illuminated.

The "motion holography" process then is utilized as follows: for example, when an acoustic string instrument is plucked the emerging waves would be frozen one-dimensionally in-time in an analogue record, tape or CD. In the second step, at a later time upon the generation of the "live" 3-D interference pattern with its simultaneous illumination, the same emerging waves are unfrozen and the released waves would then continue to proceed out from the acoustic string instrument as if it were still actually present, while long removed.

The unfrozen acoustic waves are indistinguishable from the orginal waves and the observer hears to what all appearances is the "original live performance" in full three-dimensional form.

Acoustic holography then differs from photographic holography in that the interference pattern created by two highly coherent beams is not recorded on film but it is instead generated "live" from information previously stored on a revolving disk. This advantageously removes the user from the difficult process of recording the interference pattern.

However, acoustic holography still remains a two-step process requiring first that the one-dimensional information be frozen in-time on some medium and second that two highly coherent beams of energy by interferometry decodes the one-dimensional information while being simultaneously illuminated. For example, while the technology for freezing or recording the frequency, amplitude and phase distribution of a train of one-dimensional acoustic wavefronts is long established such vinyl disk are not ordinarily viewed as "acoustic holograms" because the distance or phase information present cannot be unfrozen or decoded by conventional playback means which lacks step two.

Sterephonic sound then attempts to compensate for the lost of phase information. Such attempts however, do not address the "phase decoding problem" but instead substitutes a "stereophonic image" which does not compair favorably with the "live performance" in everyway such as a holographic or wavefront reconstructed B-D image would.

No device is known for generating, decoding and illuminating moving wave-front reconstructed 3-D acoustic holographic images from conventional analogue records, tapes and CD's.

OBJECTS OF THE INVENTION

The principle object of the present invention is to provide an acoustic wave interfering device to simultaneously generate, decode and illuminate moving three-dimensional acoustic holographic images from the frequency, amplitude and phase distribution information present on all conventional analogue records, tapes and CD's.

A second object of the present invention is to provide two highly coherent acoustic sources over a 30 to 20,000 cps frequency range so that the relative phase between the subject and reference waves remains constant in-time producing an observerable effect on the intensity distribution of the resulting interference pattern.

A third object of the present invention is to provide for the stimulated emission or wave amplication of acoustic radiation which takes place between two coherent acoustic sources when an electronic stimulating wave is divided between them triggering the stimulated emission of two identical waves, a subject acoustic wave and a reference acoustic wave with the same frequency, same direction, same phase and same polarization. The two acoustic sources therefore oscillate in unison and the two emitted waves have a definite phase relation and are said to be highly coherent. Of even greater importance is the fact that two individual waves of this type can interfere and combine constructively producing a third new wave whose amplitude is the summation of the previous two waves and is therefore an amplified wave whose radial density has been increased.

A forth object of the present invention is to provide for the reinforcement of the stimulated emission or wave amplication of acoustic radiation process by enclosing it in a tuned wideband resonator chamber.

A fifth object of the present invention is to convert the standing acoustic wave interference pattern generated where the paths of the reference and subject waves cross into a moving acoustic hologram by continuously phase modulating it with the information from a rotating analogue record, tape or CD.

A sixth object of the present invention is the retrival and preservation of the relative phase or distance information through the use of interferometry restoring this information normally lost by conventional playback means.

A seventh object of the present invention is to provide for the internal and external physical stability necessary for acoustic holography over the 30 to 20,000 cps frequency range.

An eight object of the present invention is to enlarge the beginning throat dimensions of the conventional horn so that a single corner of an average room can be utilized as a straight sided low-frequency horn powered by a moving hologram.

Another object is to provide such a device in a lightweight form so that it can be disassembled for transportation to a demonstration site.

SUMMARY OF THE INVENTION

These and other objects are achieved in an acoustic wave interfering device placed in the corner of an average room having a perpendicularly oscillating variable frequency tuning fork mounted in the rectangular mouth of a triangular shaped matched frequency wideband resonator chamber whose amplified output helps to regulate and control the frequency stability of the tuning fork by resonance.

In the preferred embodiment of the invention, the perpendicularly oscillating variable frequency tuning fork is formed by two columns or systems of acoustic dome oscillator elements attached perpendicularly to the free ends of a centrally damped flat spring mounted on an open ended boxed double fulcrum and attached to a trangular base.

The matched frequency wideband triangular resonator chamber has two parallel reflecting mirrors so that the acoustic waves can be reflected horizontally back and forth. The first mirror is located between the two perpendicularly oscillating acoustic columns where a partically reflecting hologram forms and the second mirror is fully reflecting formed by the V-shaped insides of the resonator chamber creating a wideband reflective wave amplifier whose pushpull output is also used to illuminate the hologram.

The stimulated emission of acoustic radiation occurs in the tuning fork by dividing an electronic stimulating wave between the two columns whose oscillations are continously stimulated and synchronized by an electronic amplifier coupled to and under control of a rotating modulating source over a wide range of frequencies from 30 to 20,000 cps and whose two emitted highly coherent interfering phase modulated subject and reference acoustic waves generate, decode and illuminate moving acoustic holograms from the frequency, amplitude and phase distribution information present on conventional analogue records, tapes, and CD's.

It will also be understood from the detailed description that the present invention as an interferometer builds upon U.S. Pat. No. 2,879,439 to C. H. Towns by the use of a twin system of oscillator elements, a high-Q resonator chamber and means of continuously stimulating and synchronizing the twin system of oscillator elements to create two highly coherent beams of sustained acoustic energy.

It should also be understood in the description of the circuits of the present invention as a reflective wave amplifier builds upon U.S. Pat. No. 2,929,922 to A. L. Schawlow ET AL in the use of waves which amplify by traveling back and forth between two flat parallel mirrors, one fully reflecting and one semi-transparent that is also utilized as the output port of the amplifier.

Other and further objects, advantages and features of the present invention will be understood by reference to the following specifications in conjunction with the annexed drawings, wherein like parts have been given like numbers.

DETAILED DESCRIPTION

Figure 5:
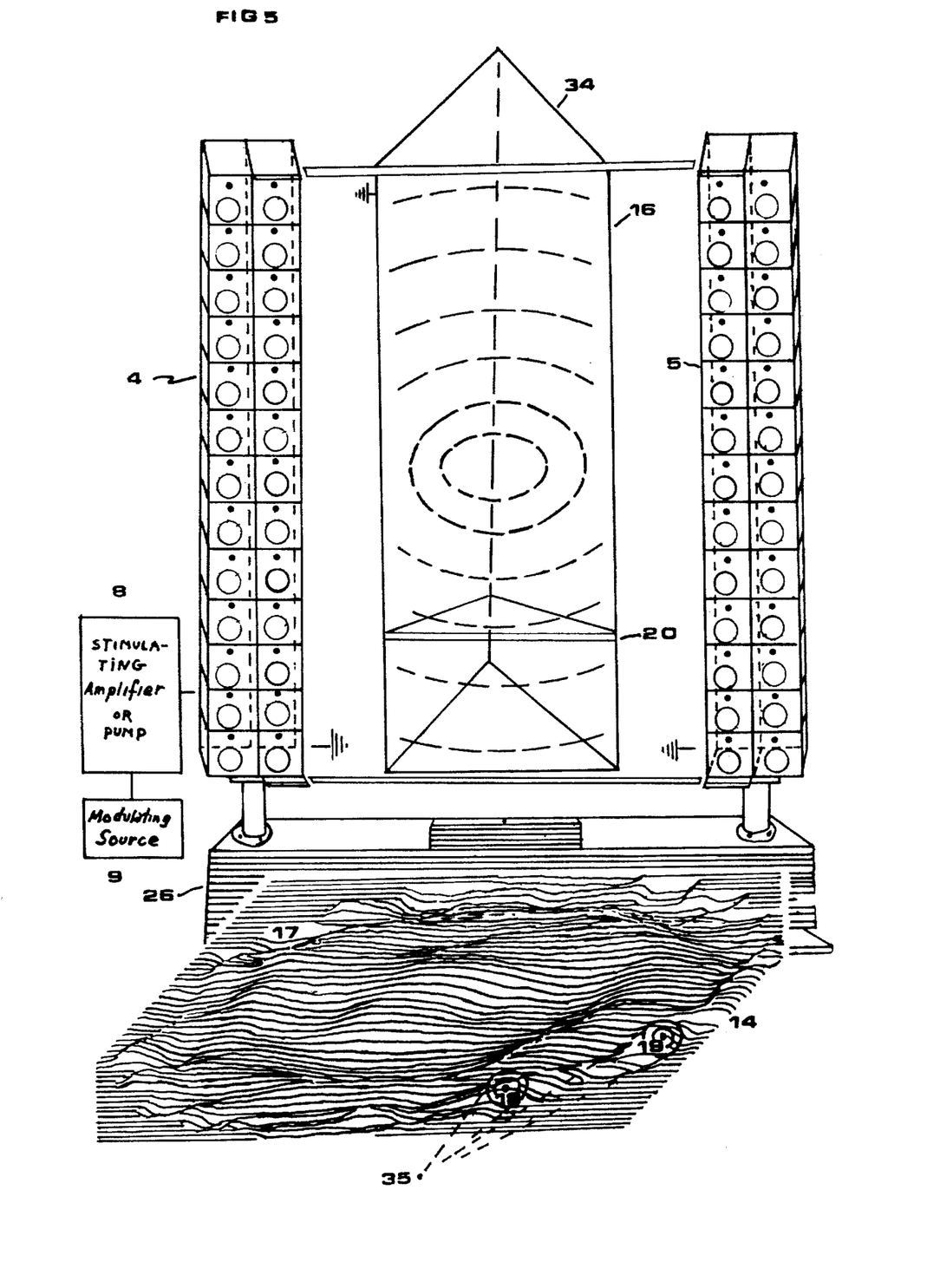
FIG. 5 shows an exploded tilted out view of the moving acoustic hologram to reveal the continuous contour generation taking place and shows a frontal view of the invention located outside of its resonator chamber.
Figure 6:
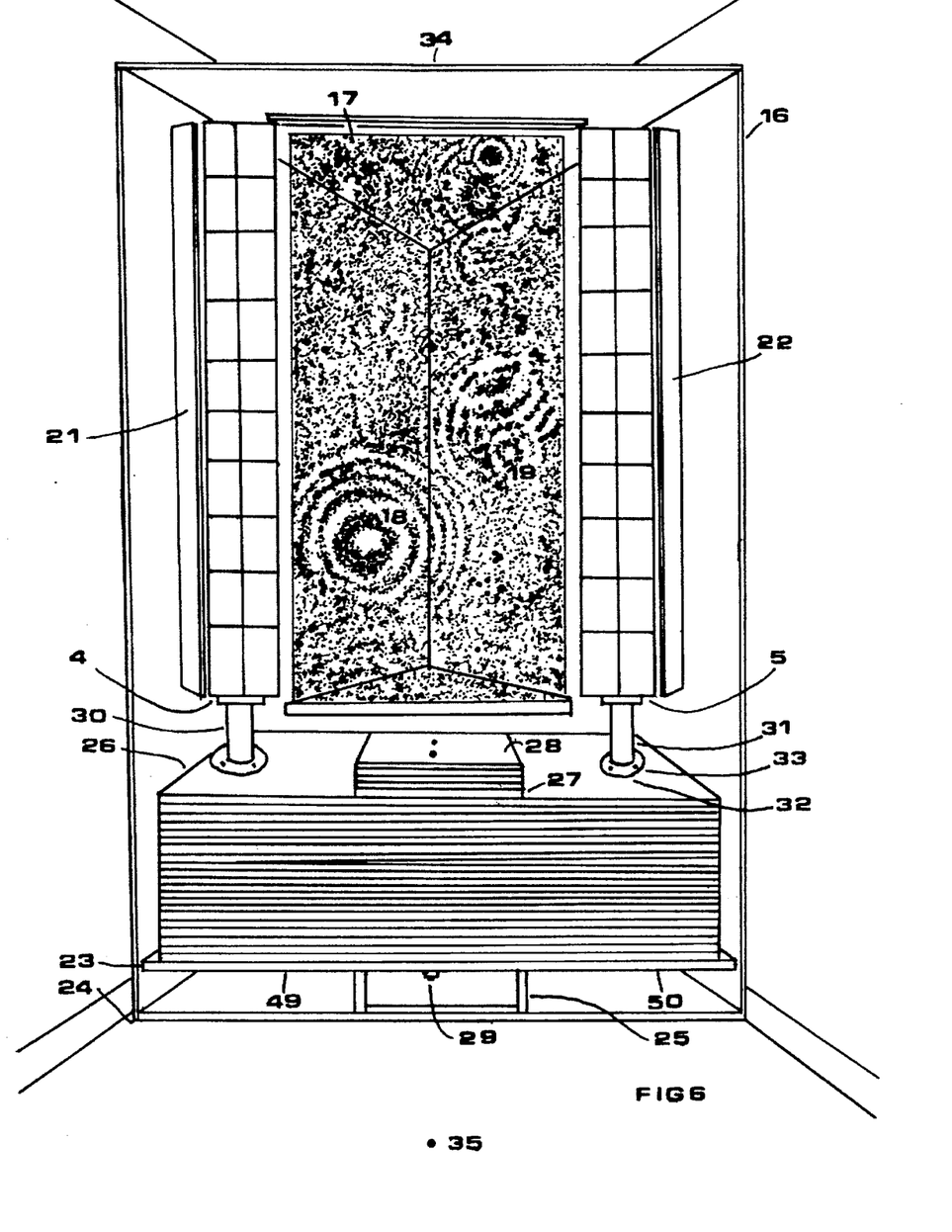
FIG. 6 shows a frontal view of the perpendicularly oscillating variable frequency tuning fork mounted in the rectangular mouth of the matched frequency resonance regulating V-shaped resonator chamber with its centrally damped flat spring suspension system.
Figure 7:
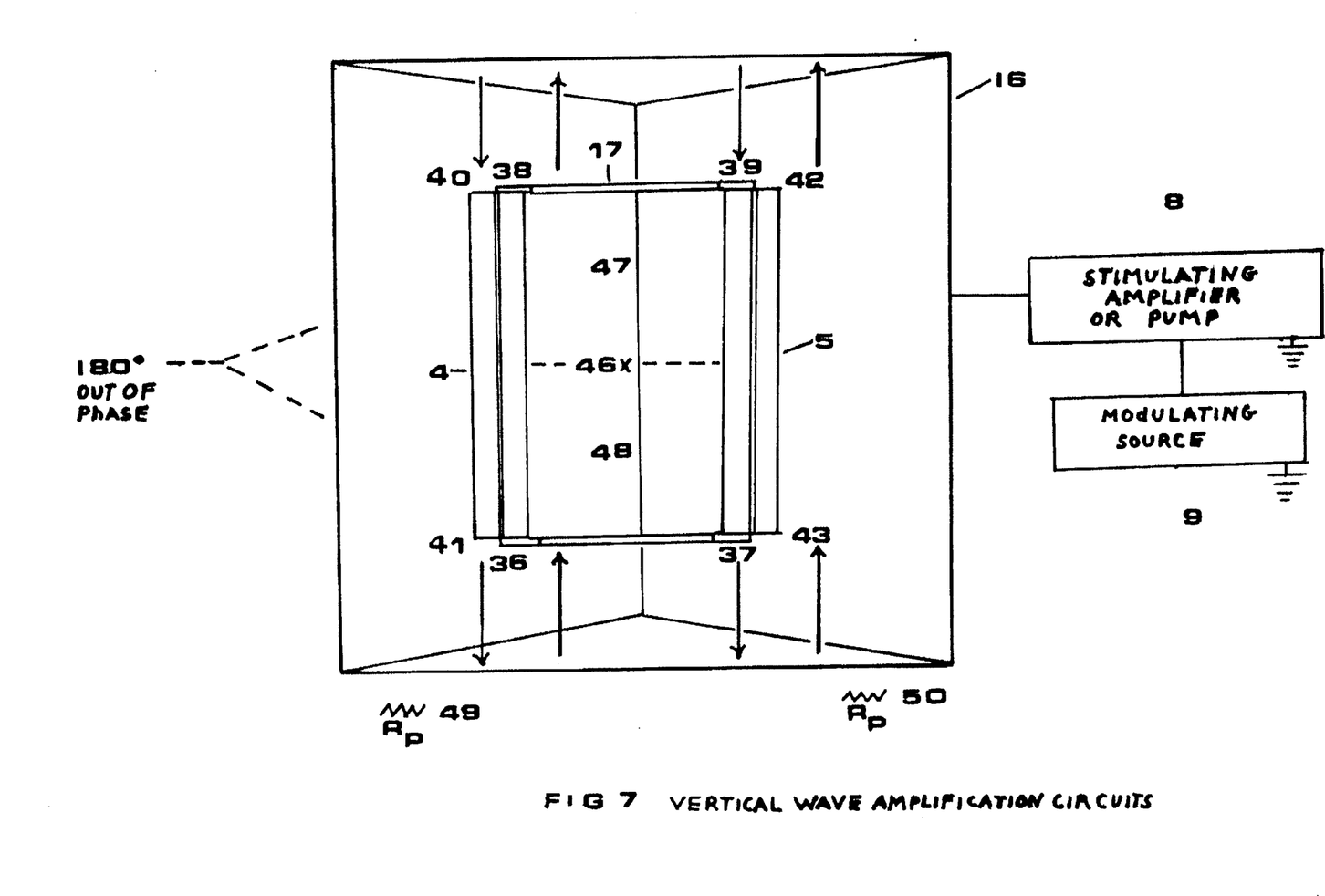
FIG. 7 shows the vertical reflective wave amplification circuits.
Figure 8:
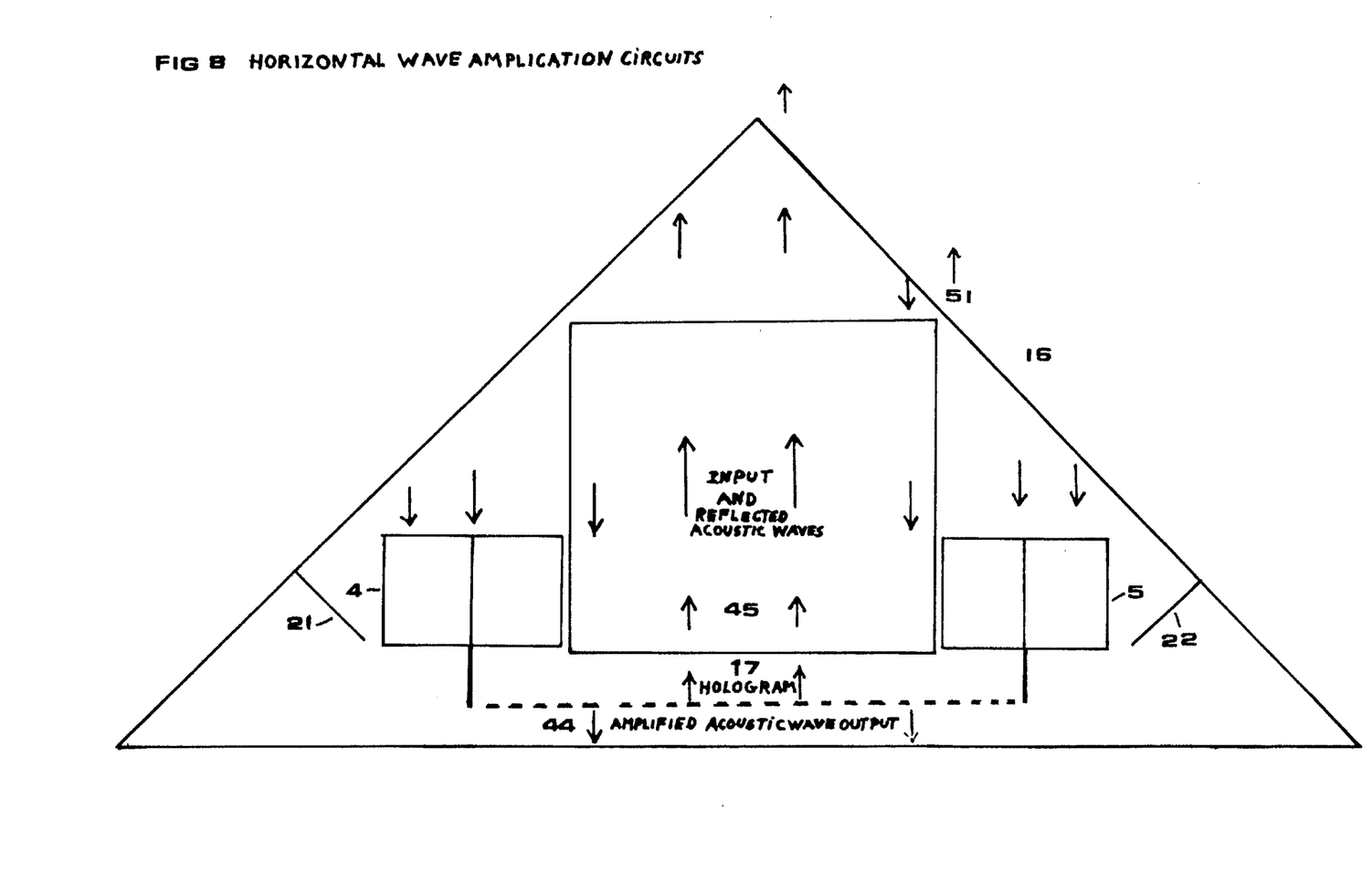
FIG. 8 shows a top view of the horizontal reflective wave amplification circuits.

FIGS. 1–4 show in highly schematic form the stimulated emission of acoustic radiation and other wave principles involved. FIGS. 5 & 6 show a perpendicularly oscillating variable frequency tuning fork formed from two columns of high and low frequency oscillating dome shaped oscillator elements mounted perpendicularly on the oscillating free ends of a centrally damped non-metalic flat spring mounted on an open ended boxed double fulcrum attached between two trangular bases mounted in the rectangular front of a matched frequency triangular shaped wideband high-Q resonator chamber or reflective wave amplifier generating, decoding and illuminating moving acoustic holograms from the frequency, amplitude and phase distribution information present on conventional analogue records, tapes and CD's. FIGS. 7 & 8 show the vertical and horizontal reflective wave amplification circuits.

Figures 1, 2, 3, 4:
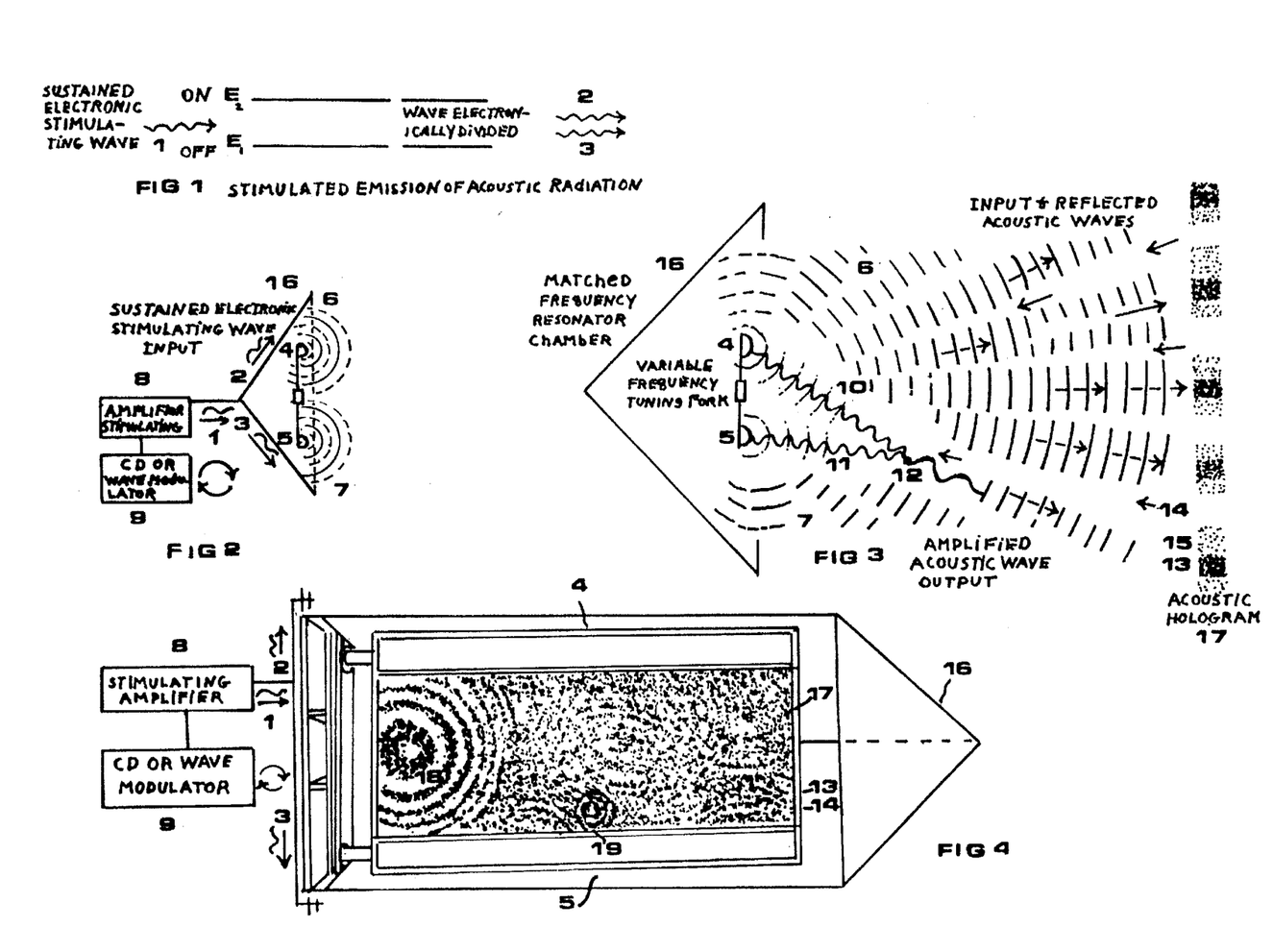
FIG. 1 shows a schematic of the stimulated emission of acoustic radiation.
FIG. 2 shows in highly schematic form a top view of two small oscillating domed shaped acoustic sources mounted on a perpendicularly oscillating tuning fork mounted in the rectangular mouth of a matched frequency wideband V-shaped resonator chamber generating phase modulated subject and reference acoustic wavefronts in-phase over a 30 to 20,000 cps frequency range.
FIG. 3 shows a larger exploded top view of two individual highly coherent phase modulated subject and reference acoustic wavefronts which travel and impring at differing angles of obliquity to produce the transparent and opaque interference frings of the acoustic hologram.
FIG. 4 shows a full schematic front view of the rectangular interference pattern of circular zone plates generated in the front of the tuned triangular matched frequency wideband V-shaped resonator chamber.

FIG. 1 at 1 shows the stimulated emission of acoustic radiation which takes place at 2 and 3 in the variable frequency tuning fork placed in the rectangular mouth of a matched frequency wideband resonator chamber. As shown in FIG. 2 the sustained electronic stimulating wave 1 from a single electronic amplifier 8 is electonically divided into two identical electronic stimulating waves 2 and 3 which then stimulate the simultaneous emissions of acoustic radiation from two acoustic dome oscillators mounted on a tuning fork at 4 and 5 generating two identical spherical acoustic waves 6 and 7.

As shown in FIG. 2 the two acoustic oscillators are a pair of small oscillating domed shaped acoustic oscillator elements 4 and 5 which emit two highly coherent phase modulated acoustic wavefronts, a subject wave 6 and a reference wave 7 in-phase over a wide range of frequencies from 30 to 20,000 cps when phase modulated by the recorded information from a rotating CD player at 9.

As shown in FIG. 3 the two acoustic dome oscillators 4 and 5 and spaced apart on the tuning fork a distance pretermined so that the individual subject and reference acoustic waves 10 and 11 generated from the two oscillators will maintain a predetermined coherency where they interfere at 12 where they can combine constructively producing a third new wave whose amplitude is the summation of the previous two waves and is therefore an amplified wave whose radiation density has been increased.

Further, as shown in FIG. 3 the directions of the individual subject and reference acoustic waves such as 10 and 11 from 4 and 5 are disposed at differing angles of obliquity from a line between the two oscillators whereby the waves interfere at predetermined distances such as 12 from the oscillators.

As shown in FIG. 3 where the subject and reference acoustic waves such as 10 and 11 arrive in-phase their combined amplitudes will add by constructive interference to produce the loud or transparent frings such as 13 which allow the traveling amplified waves such as 12 to pass through.

At other places in the interference pattern where the subject and reference waves arrive out-of-phase they will tend to cancel each other, the cancellation being complete if they are of equal amplitude. This process is called destructive interference and is responsible for all the resulting silent or reflecting frings such as 14 as shown in FIG. 3.

Where the subject and reference acoustic waves 10 and 11 as best shown in FIG. 3 at 15 are neither in nor out-of-phase the resulting sound intensity and corresponding frings are intermediate between the two extremes of 13 and 14.

Also as shown in FIG. 3 the two oscillator elements 4 and 5 are overlapping axis of revolution for the infinite numbers of individual coherent waves such as 10 and 11 in the two phase modulated spherical wavefronts 6 and 7.

This wave summation amplification process as shown in FIG. 3 at 12 is then continued by adding additional oscillator elements to 4 and 5 forming them into two columns or populations. As shown in FIG. 5 at 4 and 5 each additional oscillator element is comprised of a high and low frequency oscillator housed in an individual aluminum airtight comparment painted black and wired in-phase with one another. Each individual oscillator element is then aligned with the other so that the summation of all of the acoustic waves emitted at 6 and 7 have the same frequency, same direction, same phase and same polarization. Each additional oscillator element added to 4 and 5 represents an additional stage of wave amplification which then is a function of the population of oscillators in the two columns of the tuning fork.

As this wave summation amplification process continues as shown in FIGS. 2, 3 & 5 the electronic wave slpitting causes the distance 4 and 5 travels during its oscillations to decrease until only microscopic oscillations occur allowing the number of oscillations it produces per second to greatly increase.

As shown in FIGS. 5 & 6 this wave summation amplification process is then enhanced by placing the black absorbing tuning fork formed of two columns of oscillator elements 4 and 5 mounted on a flat spring 26 in the rectangular mouth of a tuned triangular wideband resonator cavity 16.

As shown in FIGS. 3 & 4 by virtue of the summated phase modulated spherical wave 6 interfering with the summated phase modulated reference spherical wave 7 each audible point of a 3-D scene forms from the recorded information at 9 its own circular zone plate in the interference pattern 17 such as 18 and 19.

As best shown in FIGS. 3, 5 & 6 the two acoustic oscillator columns 4 and 5 are disposed in the rectangular front of a tuned triangular wideband V-shaped resonator chamber 16 and so positioned relative to each other that the highly coherent phase modulated subject and reference acoustic waves contained in the two acoustic wavefronts 6 and 7 tend to interfere constructively and destructly with each other to form a rectangular interference pattern of circular zone plates as shown at 17 which can be regarded as a three-dimensional rectangular analogue of a sinusoidal wave produced by a pair of oscillators.

The phase modulated acoustic hologram as shown in FIG. 5 made in the manner just described then has many of the properties of a moving acoustic diffraction grading 17 with the phase modulated out-of-phase acoustic waves such as 14 produced by a rotating CD player at 9 constructing continuously changing contours.

As shown in FIG. 5 the high-Q cavity 16 is tuned by varying its length by means of a sliding mirrored end section in the floor of the cavity as shown at 20. The length of the chamber 16 is tuned to the wideband of frequencies produced by the oscillations of 4 and 5 where-in the chamber's length is substantially greater than its width.

As shown in FIG. 6 for purposes of illustration, the large moving acoustic hologram at 17 forms between the insides of the two columns 4 and 5. This also forms the throat area of a conventional horn so that a single corner of an average room can be utilized as a straight sided low-frequency horn. For proper efficiency, the throat dimensions of the horn must be smaller than the total diameters of the two oscillator columns at 4 and 5. As shown in FIG. 6 this is accomplished by providing two long slots along 21 and 22 for the air moved by the hologram to pass through.

As shown in FIG. 6 the internal and external physical stability necessary for acoustic holography is provided by a large damped flat spring and tuned metal weight suspension system comprising: two rigid triangular bases 23 and 24 attached between an open ended boxed double fulcrum 25 with a large pressboard spring 26 stacked on top which is clampled between a metal plate 27 and the fulcrum. Metal tuning weights 28 are also attached at the center all bolted together with long threaded rods 29.

Also as shown in FIG. 6 the two metal post 30 and 31 set the length of the resonator chamber and are attached to the bottom of the oscillator columns at 4 and 5 and to the top of the spring 26 with metal flages at 32 and are also attached by long threaded rods as shown at 33.

The recoil forces from the two systems of high speed oscillators 4 and 5 are transmitted down the two metal post at 30 and 31 to the dampened flat spring suspension system at 26 where the work necessary to bend the spring downward over the double fulcrum at 25 and move the weights upward at 28 absorbs most of their linear momentum while giving the two columns 4 and 5 a stable ride when tuned to the systems proper oscillating frequency. The roof as shown in FIG. 6 at 34 is attached to the resonator walls and does not move with the suspension system.

As shown in the interference pattern in FIGS. 3, 5 & 6 the resulting multitudes of illuminating in-phase acoustic waves such as 12 passing through the circular zone plates such as 18 and 19 in the acoustic hologram 17 then converge toward the same focal point according to the phase modulation from 9 thereby reconstructing the virtual image of the orginal live performance. As shown in FIGS. 5 & 6 the multitudes of illuminating acoustic waves converging through the zone plates such as 18 and 19 produce at least one virtual three-dimensional acoustic image from the zero order waves which can be viewed from a central focal point at 35 about six feet away.

As shown in FIG. 6 the cavity 16 has highly reflecting walls so that the acoustic waves can be relected back and forth horizontally between the space formed by the two acoustic columns where a partially reflecting hologram 17 forms and the mirrored insides of the V-shaped resonator chamber 16 creating a wideband reflective wave amplifier whose push-pull output is used to illuminate the hologram.

Also as shown in FIG. 7 the vertical circuits provide additional gain in the reflective wave amplifier where the inner columns form the primary oscillator circuits which reflect the acoustic waves back and forth vertically in front of the columns with fully reflecting parallel mirrors located at 36 and 37 and partially reflecting mirrors at 38 and 39.

The outer columns 40,41 and 42,43, then form the reflective wave amplifier's isolator circuits with no column end mirrors which are activated by drone waves which extend over from the oscillator circuits.

As shown in FIG. 7 strip mirrors are run from the rectangular corner point of the hologram 38 to 39, 36 to 37, 37 to 39 and 36 to 38 to form a wave generated rectangular hologram that seals the output port of the reflective wave amplifier 17 to the front of the high-Q chamber 16.

Also as shown in FIG. 8 the hologram 17 is partially transparent a fraction of the radiation 44 being emitted from the high-Q cavity 16 and a fraction 45 being reflected back into the chamber.

The maxium value of the peakpower of the reflective wave amplifier's output is partially a function of the degree of the reflectivity of the acoustic hologram whose thickness is adjusted by the width of the strip mirrors as shown at 38,39 and 36,37 in FIG. 7. The thicker the acoustic hologram the more reflectivity and feedback but the less output. On the other hand, the thinner the hologram the more transparent and the higher the output. The maxium peak power output occuring at about one-sixtyfourth of an inch or about the same thickness if the hologram were recorded on a fixed film medium.

Further, by increasing the thickness of the sidewalls of the open ended boxed double fulcrum as shown in FIG. 6 at 25 the number of oscillations per second produced by the recoil forces at 4 and 5 increases and the size and definition of the acoustic image increases.

Even more remarkable then is that the acoustic hologram as a reflective acoustic source as shown in FIG. 6 at 17 can be utilized to provide additional gain by moving it perpendicularly up and down. As a moving acoustic source the acoustic hologram 17 has an acoustic center as shown in FIG. 7 at 46. When the acoustic hologram is accelerated upward the acoustic waves in the top half of the hologram at 47 are more closely crowed together while the acoustic waves in the bottom half 48 are stretched out further behind. Therefore, the reflected gain from the top half of the acoustic hologram 47 increases while the reflected gain from the bottom half 48 decreases, the total gain in the horizontal reflective wave circuit is then additive owning to its push-pull action forming a high gain circuit which is a function of the number of perpendicular oscillations per second. When the proper resistance is added to the horizontal circuit at 49 and 50 as shown in FIGS. 6 & 7 sound of remarkable purity exits the output port at 44 as shown in FIG. 8.

Further, as shown in FIG. 8 the acoustic waves reflected from the partially transparent hologram at 45 form the input at the mouth of the resonator chamber.

Also as shown in FIG. 8 the tunneling or escaping acoustic energy losses through the walls of the enclosed cavity 16 must be carefully controlled by the use of metal mirrors at least one-forth of an inch thick to establish a "high-Q" since the quality or Q factor of the resonator chamber is defined by:

$$Q = 2\pi V \frac{\text{energy stored per second}}{\text{energy lost per second}}$$

Therefore, an increase in the acoustic energy stored means the strength of the trapped oscillating acoustic field 45 as shown in FIG. 8 in the chamber increases. This is important because the frequency stability of the oscillating acoustic field 45 is of a very high order and as its strength increases it imposes by resonance some of its frequency stability back upon the oscillations of the tuning fork and its twin system of acoustic oscillator elements at 4 and 5 as shown in FIG. 8.

However, acoustic energy lost per second means energy lost through the walls as shown at 51 in FIG. 8 which if larger than the gain causes the operation of the reflective wave amplifier to become unstable or cease. Further, reflection losses occur between the mirrors in their parallel alignment and diffraction according to the size of their surface areas, all effect the wave amplifiers operation.

The necessary and sufficient conditions to do acoustic holography can then be summated as follows:

means to provide for connecting said oscillator columns to the ends of said spring as shown in FIG. 6 at 30,31 and 32.

means to provide for aligning, clamping and damping said spring to the double fulcrum mounted on a triangular base as shown in FIG. 6 at 29 and 33.

means to provide for continuously stimulating, synchronizing and phase modulating said columns over a 30 to 20,000 cps frequency range as shown in FIG. 5 at 8,9.

means to provide for increasing the number of oscillations produced per second by an individual oscillator element in said columns as shown in FIG. 5 by the stacked oscillator elements at 4 and 5.

means to provide for adjusting the height of said oscillator columns as shown in FIG. 6 by the length of 30 and 31.

means to provide for the electronic division of a single electronic stimulating wave into two identical electronic stimulating waves with the same frequency, same direction, same phase, and same polarization as shown in FIG. 2 at 2 and 3.

means to provide electrical connections to said acoustic oscillator columns as shown in FIG. 5 at 4 and 5.

means to provide for reflecting the acoustic waves vertically back and forth in front of the inner oscillator columns and differentiating the input from the output and extrating energy from said circuits as shown in FIG. 7 at 36,38 and 37, 39.

means to provide for activating the outer oscillator's columns which form the reflective wave amplifier's isolator circuits as shown in FIG. 7 at 40,41 and 42,43 which are activated by drone waves which extend over from the inner oscillating circuits.

means to provide to adjust the distance between said oscillator columns so that when placed in the corner of an average room their respective highly coherent subject and reference waves emitted interfere with each other to form a moving rectangular interference pattern of circular zone plates one for each audiable point in a 3-D scene as shown in FIG. 6 at 30 and 31.

means to provide for controlling the direction of the individual spherical wavefronts generated so that the two high and low frequency oscillator columns can be disposed at differing angles of obliquity from a line between the two oscillator columns, whereby the coherent phase modulated subject and reference waves generated interfere at a predetermined distance from the oscillators where they simultaneously impring to produce a rectangular interference pattern of circular zone plates one for each audiable point in a 3-D scene as shown in FIG. 6 threaded pipe ends at 30 and 31.

means to provide for stacking the oscillator elements in columns not shown in FIG. 6 at 4 and 5 metal straps on the backs of the columns.

means to provide for mounting said tuning fork in the rectangular mouth of said chamber as shown in FIG. 6 at 23,24 and 25.

means to provide for tuning the length of said resonator chamber to the wide range of frequencies produced by said oscillator columns as shown in FIG. 5 at 20.

means to provide for reflecting the acoustic waves horizontally back and forth in the resonator chamber and differentiating the input from the output of the horizontal circuit of the reflective wave amplifier and extrating energy from said circuit as shown in FIG. 8 as 16 and 17.

means to provide to regulate the oscillations of said tuning fork by resonance or forced resonance as shown in FIG. 8 at 4 and 5.

means to provide for adding resistance to the push-pull horizontal circuit as shown in FIG. 7 at 49 and 50.

means to provide to stabilize the 3-D acoustic image over a 30 to 20,000 cps frequency range as shown in FIG. 6 at 26.

means to provide for the hologram's use as a partially transparent end mirror and output port that seals the front of the high-Q chamber and determines the thickness of the said moving hologram as shown in FIG. 7 at 38,39,36 and 37.

means to provide the moving hologram's use to drive a straight-sided corner horn as shown in FIG. 6 at 17.

means to provide for control of the impedence of the corner horn as shown in FIG. 6 at 21,22 and 49,50.

means to provide for the control of the air movement generated by the moving hologram's motion as shown in FIG. 6 at and 22.

means to provide to enhance the absorption of the reflective wave amplifier's output by the said oscillator column's as shown in FIG. 5 the black columns at 4 and 5.

means to provide for transferring acoustic energy radiated by said oscillator columns to said horizontal and vertical circuits as shown in FIGS. 7 & 8 the mirrors at 36,38, 37,39 and 16,17.

means to provide for adjusting the thickness of the sidewalls of the open ended boxed double fulcrum whereas the number of oscillations per second produced by the recoil forces increases and the size and definition of the acoustic image increases as shown in FIG. 6 at 25.

means to provide for stabilizating the tops of the two said oscillator columns a system of wire and tension rod not shown.

means to provide for phase-inverting the hologram as shown in FIG. 7 the perpendicular oscillations at 4 and 5.

The foregoing description of the preferred embodiment of the invention has been presented for the purpose of illustration and description. It is not intended to be exhaustive or to limit the invention to the precise form disclosed. Many modifications and variations are possible in the light of the above teaching. It is intended that the scope of the invention be limited not by this detailed description, but rather by the claims appended hereto.

What is claimed is:

1. An acoustic wave interfering device for use in generating, decoding and illuminating moving acoustic holograms from the frequency, amplitude and phase distribution information present on conventional analogue records, CD's and tapes comprising a perpendicularly oscillating variable frequency tuning fork formed from two columns of high and low frequency oscillating dome shaped oscillator elements mounted perpendicularly on the oscillating free ends of a centrally damped non-metalic flat spring mounted on an open ended boxed double fulcrum attached between two triangular bases; and means to provide for connecting said oscillator columns to the ends of said spring; and means to provide for aligning, clamping and damping said spring to the double fulcrum mounted on a triangular base; and means to provide for continuously stimulating, synchronizing and phase modulating said columns over a 30 to 20,000 cps frequency range; and means to provide for increasing the number of oscillations produced per second by an individual oscillator element in said columns; and means to provide for adjusting the height of said oscillator columns; and means to provide for the electronic division of a single electronic stimulating wave into two identical electronic stimulating waves with the same frequency, same direction, same phase, and same polarization; and means to provide electrical connections to said acoustic oscillator columns; and means to provide for reflecting the acoustic waves vertically back and forth in front of the inner oscillator columns and differentiating the input from the output and extrating energy from said circuits; and means to provide for activating the outer oscillator's columns which form the reflective wave amplifier's isolator circuits; and means to provide to adjust the distance between said oscillator columns so that when placed in the corner of an average room their respective highly coherent subject and reference waves emitted interfere with each other to form a moving rectangular interference pattern of circular zone plates one for each audiable point in a 3-D scene; and means to provide for controlling the directions of the individual spherical wavefronts generated so that the two high and low frequency oscillator columns can be disposed at differing angles of obliquity from a line between the two oscillator columns, whereby the coherent phase modulated subject and reference waves generated interfere at a predetermined distance from the oscillators where they simultaneously impring to produce a rectangular interference pattern of circular zone plates one for each audiable point in a 3-D scene;

means to provide for stacking the oscillator elements in columns; and a matched frequency triangular shaped wideband high-Q resonator chamber or reflective wave amplifier; and means to provide for mounting said tuning fork in the rectangular mouth of said chamber; and means to provide for tuning the length of said resonator chamber to the wide range of frequencies produced by said oscillator columns; and means to provide for reflecting the acoustic waves horizontally back and forth in the resonator chamber and differentiating the input from the output of the horizontal circuit of the reflective wave amplifier and extrating energy from said circuit; and means to provide to regulate the oscillations of said tuning fork by resonance or forced resonance; and means to provide for adding resistance to the push-pull horizontal circuit; and means to provide to stabilize the 3-D acoustic image over a 30 to 20,000 cps frequency range; and a wave generated hologram; and means to provide for the hologram's use as a partially transparent end mirror and output port that seals the front of the high-Q chamber and determines the thickness of the said moving hologram; and means to provide the moving hologram's use to drive a straight-sided corner horn; and means to provide for control of the impedence of the corner horn; and means to provide for the control of the air movement generated by the moving hologram's motion; and means to provide to enhance the absorption of the reflective wave amplifier's output by the said oscillator column's and means to provide for transferring acoustic energy radiated by said oscillator columns to said horizontal and vertical circuits; and means to provide for adjusting the thickness of the sidewalls of the open ended boxed double fulcrum whereas the number of oscillations per second produced by the recoil forces increases and the size and definition of the acoustic image increases; and means to provide for stabilizating the tops of the two said oscillator columns; and means to provide for phase-inverting the hologram.

2. The apparatus of claim 1 wherein said acoustic oscillator elements comprise a system of manufactured electrodynamic small dome shaped oscillator elements or acoustic transducers.

3. The apparatus of claim 1 where-in the said means for regulating the frequency stability of the acoustic waves generated is the matched frequencies of the tuning fork and resonator chamber so that the higher order amplified waves impose by resonance their correctness to the tuning fork.

4. The apparatus of claim 1 where-in the said triangular wideband matched frequency V-shaped chamber has a sliding mirrored floor section for tuning the length of the high-Q cavity.

5. The apparatus of claim 1 where-in said acoustic columns means for continuously stimulating and synchronizing is an electronic amplifier.

6. The apparatus of claim 1 where-in said means for continuously stimulating and synchronizing said columns is coupled to and under control of a rotating modulating source.

7. The apparatus of claim 1 where-in said distance between the two said oscillator columns is predetermined so that the acoustic wavefronts generated from the respective said columns maintains a predetermined coherency where they intersect and combine constructively producing a third new wave whose amplitude is the summation of the previous two waves and is therefore an amplified wave which travels through a transparent fring.

8. The apparatus of claim 1 where-in said distance between the two said oscillator columns is predetermined so that the acoustic wavefronts generated from the respective said columns maintains a predetermined coherence where they intersect and combine distructively producing an opaque reflecting fring.

9. The apparatus of claim 1 where-in the said rectangular interference pattern of circular zone plates has one for each audiable point in a 3-D scene.

10. The apparatus of claim 1 where-in the said interference pattern the intersection of the illuminating highly coherent in-phase acoustic waves passing through the multitude of transparent and opaque circular zone plates in the rectangular acoustic hologram produces at least one virtual three-dimensional acoustic image.

11. The invention according to calim 1 where-in said means for stabilizing the three-dimensional acoustic image comprises a centrally damped flat spring and metal weight suspension system attached to two perpendicularly oscillating acoustic columns tuned to the said spring and resonator chamber's proper oscillating frequency to provide sufficient external and internal damping of the recoil forces generated over the 30 to 20,000 cps frequency range.

12. The invention according to claim 1 where-in said means for stabilizing the tops of the two said oscillator columns is a lightweight system of wire and tension rod.

13. The invention according to claim 1 where-in said means for phase-inverting is the perpendicular oscillations of the said hologram.

14. The invention according to claim 1 where-in said means for decoding the hologram is by interferometry of the two oscillating acoustic columns.

15. The invention according to claim 1 where-in said means for increasing the number of oscillations produced per second by an individual oscillator element in said columns is to replace the air with a silicone gel.

* * * * *